(12) United States Patent
Anderson et al.

(10) Patent No.: US 10,779,812 B2
(45) Date of Patent: Sep. 22, 2020

(54) DEVICES AND METHODS FOR SUTURE PLACEMENT

(71) Applicant: Dura Tap LLC, Wayne, PA (US)

(72) Inventors: David Greg Anderson, Moorestown, NJ (US); Mark F. Kurd, Bryn Mawr, PA (US); Jay Tapper, Wayne, PA (US); Jens Johnson, Austin, TX (US)

(73) Assignee: Durastat LLC, Wayne, PA (US)

( * ) Notice: Subject to any disclaimer, the term of this patent is extended or adjusted under 35 U.S.C. 154(b) by 344 days.

(21) Appl. No.: 15/654,878

(22) Filed: Jul. 20, 2017

(65) Prior Publication Data
US 2019/0021723 A1     Jan. 24, 2019

(51) Int. Cl.
| | |
|---|---|
| *A61B 17/04* | (2006.01) |
| *A61B 17/28* | (2006.01) |
| *A61B 17/062* | (2006.01) |
| *A61B 17/06* | (2006.01) |

(52) U.S. Cl.
CPC ...... *A61B 17/0469* (2013.01); *A61B 17/0401* (2013.01); *A61B 17/0482* (2013.01); *A61B 17/062* (2013.01); *A61B 17/2841* (2013.01); *A61B 17/06061* (2013.01); *A61B 2017/06095* (2013.01); *A61B 2017/06142* (2013.01)

(58) Field of Classification Search
CPC ...... A61B 2017/06142; A61B 17/0469; A61B 2017/047; A61B 17/062; A61B 17/0482; A61B 17/0401
See application file for complete search history.

(56) References Cited

U.S. PATENT DOCUMENTS

| | | | |
|---|---|---|---|
| 5,387,221 A * | 2/1995 | Bisgaard | A61B 17/0469 112/169 |
| 5,741,277 A | 4/1998 | Gordon | |
| 7,993,354 B1 * | 8/2011 | Brecher | A61B 17/0482 606/145 |
| 2005/0251210 A1 * | 11/2005 | Westra | A61B 17/0401 606/232 |
| 2009/0024145 A1 * | 1/2009 | Meade | A61B 17/0482 606/144 |
| 2014/0296880 A1 | 10/2014 | Heneveld | |

OTHER PUBLICATIONS

International Search Report filed in PCT/US2018/042652 dated Oct. 11, 2018.

* cited by examiner

*Primary Examiner* — Shaun L David
*Assistant Examiner* — Christina C Lauer
(74) *Attorney, Agent, or Firm* — Rankin, Hill & Clark LLP

(57) ABSTRACT

A suturing device includes an elongate body, a needle holder, an actuator, a needle and a needle retainer. The needle holder extends away from a distal end portion or is provided as part of the distal end portion of the elongate body. The needle holder includes a distal end section having a distal-most tip, and defines a needle passage and a distal opening adjacent the distal-most tip. The actuator is operable between a first operating position and a second operating position. Movement of the actuator from the first operating position toward the second operating position moves the needle in an advance direction. The needle is in the needle passage. The needle retainer engages the needle holder and the needle when the actuator is in the first operating position and inhibits movement of the needle toward distal opening while the actuator is in the first operating position.

14 Claims, 13 Drawing Sheets

DEVICES AND METHODS FOR SUTURE PLACEMENT

BACKGROUND

The present disclosure relates generally to surgery and the placement of sutures, and more particularly, to devices and methods for the suture repair of tissue.

Surgical closure techniques using sutures is one approach to tissue repair. In some instances, however, these techniques can be difficult to execute due to anatomic constraints, obstruction of visualization by blood or other bodily fluids, and the proximity to nerve rootlets. In some instances, these challenges can be further complicated when using minimally invasive techniques such as, for example, a tubular retractor. Traditional tools and devices can be limited and, in some instances, lack maneuverability to avoid obstructions and/or to enable adequate passage of the needle and suture through the tissue.

SUMMARY

In view of the foregoing a suturing device includes an elongate body, a needle holder, an actuator, a needle and a needle retainer. The elongate body includes a proximal end portion and a distal end portion. The needle holder extends away from the distal end portion or is provided as part of the distal end portion. The needle holder includes a distal end section having a distal-most tip. The needle holder defines a needle passage and a distal opening adjacent the distal-most tip. The needle is in the needle passage and includes a first end, which is pointed, and a second end, which is opposite the first end. The actuator interacts with the elongate body and is operable between a first operating position and a second operating position. The actuator is configured such that movement of the actuator from the first operating position toward the second operating position moves the needle in an advance direction. The needle retainer engages the needle holder and the needle when the actuator is in the first operating position and is configured to inhibit movement of the needle toward distal opening while the actuator is in the first operating position.

DETAILED DESCRIPTION

Figure 1:
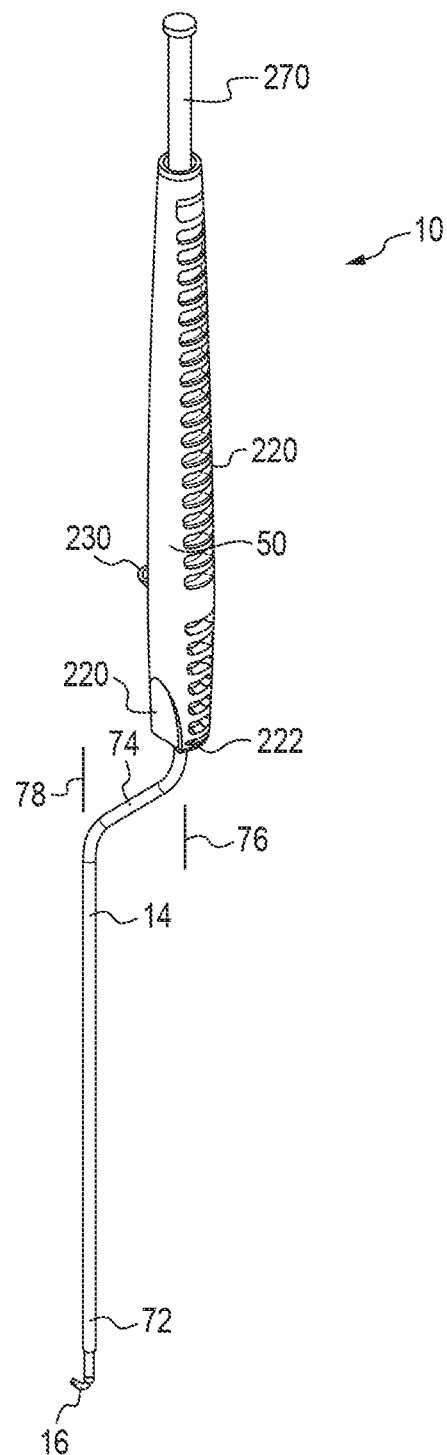
FIG. 1 is a perspective view a suturing device.
Figure 2:
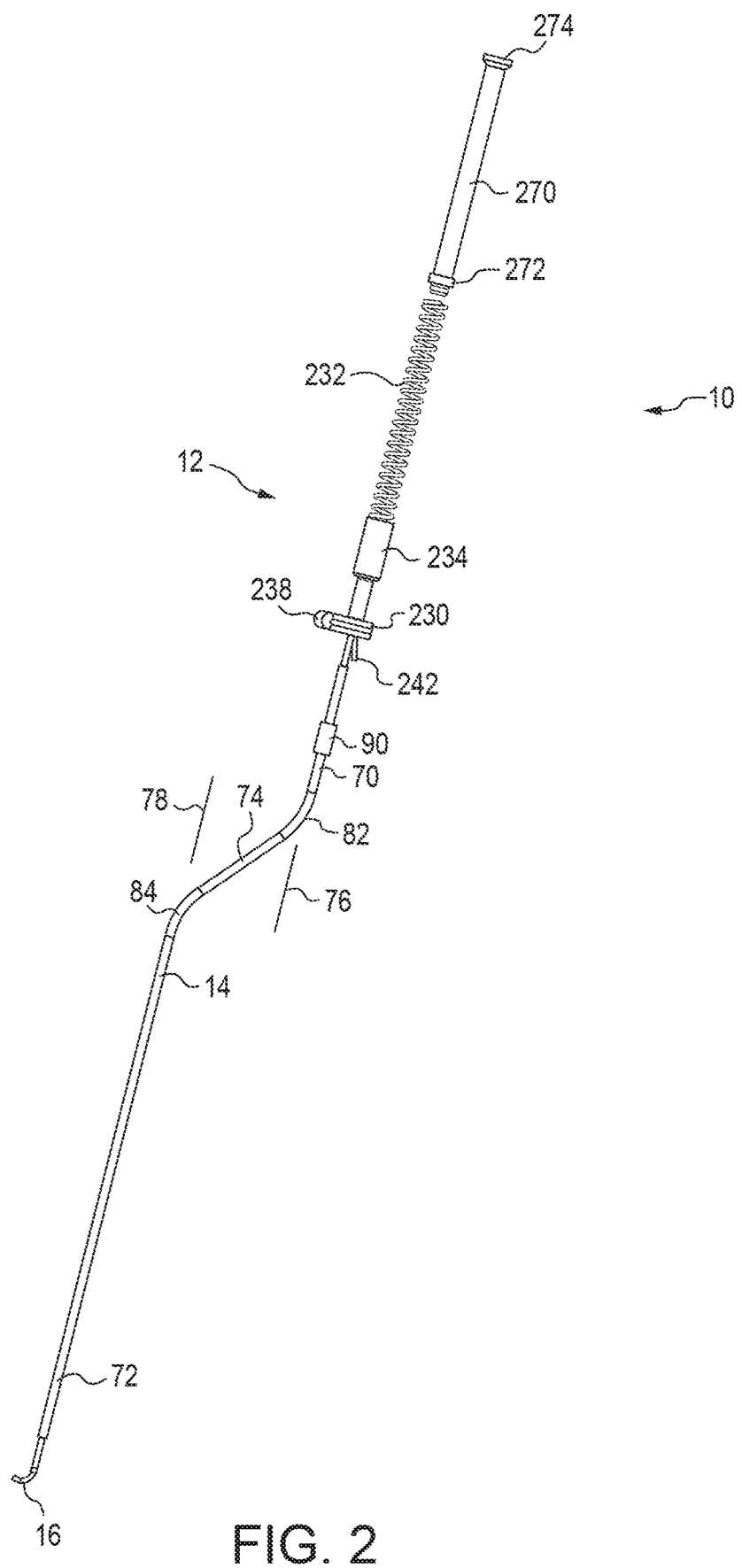
FIG. 2 is a perspective view the suturing device of FIG. 1 with a handle removed to show components of an actuator.
Figure 3:
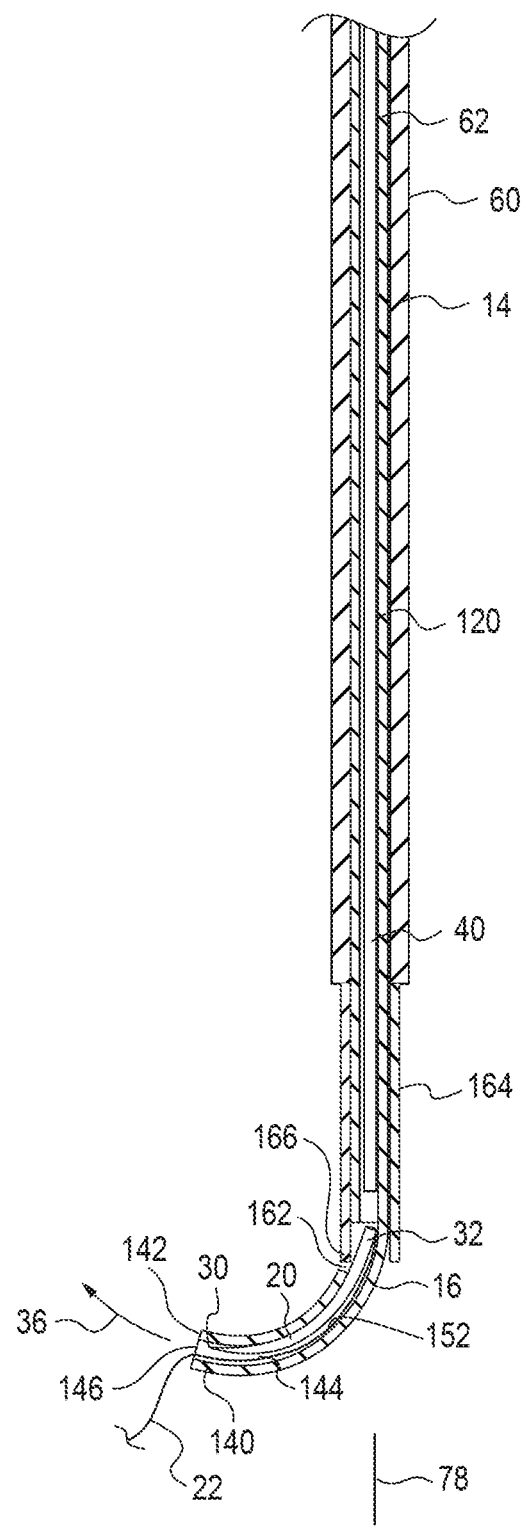
FIG. 3 is a cross-sectional view of a lower portion of the suturing device of FIG. 1.

FIG. 1 depicts an example of a suturing device 10 that is useful to suture tears in tissue and that can be used in many different types of surgical procedures. With reference to FIG. 2, the suturing device 10 generally includes an actuator 12, an elongate body 14, and a needle holder 16. The suturing device 10 is particularly useful during a minimally invasive surgical procedure that is performed through a tubular retractor or other small surgical portal to accurately locate a needle 20 and a suture 22, which are shown in FIG. 3, to facilitate passing the needle 20 through target tissue to be sutured.

The needle 20 in the illustrated embodiment is a curved needle having a first end 30, which is pointed, and a second end 32, which is opposite to the first end 30. The needle 20 can be similar to commercially available curved needles made from known materials. The needle 20 could also be formed from a malleable, or flexible, material such that the needle 20 could follow a curve when positioned within the needle holder 16, which is curved, and then later straighten after exiting the needle holder 16. Both the needle holder 16 and the needle 20 can take other configurations, such as straight.

Actuation of the actuator 12 moves the needle 20 in an advance direction 36 with respect to the needle holder 16. The needle 20 moves from a retracted position, which is shown in FIG. 3, to a released condition in which the needle 20 is released from the needle holder 16. When in the released condition, the surgeon can grasp the needle 20, for example with forceps, and pull the needle 20 and the suture 22. The suture 22 connects with the needle 20 and extends from the second end 32 of the needle 20. The suture 22 can be swaged to the second end 32 of the needle 20. The suture 22 can also connect with the needle 20 in other conventional manners. The suture 22 can be acquired from known suture manufacturers.

The actuator 12 is operable between a first operating position and a second operating position. Movement of the actuator 12 from the first operating position toward the second operating position moves the needle 20 in the advance direction 36 with respect to the needle holder 16 thus moving the needle 20 toward the released condition in which the needle 20 is released from the needle holder 16. In the illustrated embodiment, the actuator 12 includes a flexible section, which in the illustrated embodiment is made up of a wire 40, which can be made from nitinol. The flexible section is configured to bend within the needle holder 16 when the actuator 12 is moved from the first operating position toward the second operating position. The other components of the actuator 12 will be described in more detail below.

The elongate body 14 connects with a handle 50 in the illustrated embodiment. The elongate body 14 in the illustrated embodiment is in the form of a cannula. The elongate body 14 has an outer surface 60, which is smooth, and defines a track 62 that receives a portion of the actuator 12, more particularly the wire 40 in the illustrated embodiment. As described above, the elongate body 14 is a cannula and the track 62 is a lumen that receives the wire 40 of the actuator 12. The track 62 need not encircle the wire 40, but could be U-shaped. In the depicted embodiments, the elongate body 14 is circular in a cross section taken normal to the longest dimension of the elongate body 14, however, the elongate body 14 could take alternative configurations, such as polygonal or U-shaped.

The elongate body 14 has a bayonet configuration in the illustrated embodiment; however, the elongate body 14 could take alternative configurations, such as straight along a longitudinal axis. The elongate body 14 includes the proximal end portion 70 and a distal end portion 72 connected by an intermediate portion 74. The proximal end portion 70 connects with the handle 50 in a manner that will be described in more detail below. In the illustrated embodiment, the needle holder 16 is received in and connected with the elongate body 14 and extends away from the distal end portion 72. Alternatively, the needle holder 16 can be provided as part of the distal end portion 72 of the elongate body 14. The elongate body 14 is made from a rigid metal material; however, if desired at least a portion of the elongate body 14 may be made from a malleable or flexible material to allow the surgeon to bend at least a portion of the elongate body 14 into a desirable configuration for insertion into an animal body during a surgical procedure. In the illustrated embodiment, an outer diameter of the elongate body 14 is constant between the proximal end portion 70 and the distal end portion 72. The outer diameter can be less than 3.5 mm, which provides a very slim device to enhance the line of sight for a surgeon during the surgical procedure.

The intermediate portion 74 is positioned between the proximal end portion 70 and the distal end portion 72. The proximal end portion 70 extends along a proximal end portion longitudinal axis 76. The distal end portion 72 extends along a distal end portion longitudinal axis 78, which is offset from the proximal end portion longitudinal axis 76 in a forward direction. In the illustrated embodiment, the distal end portion longitudinal axis 78 is offset from the proximal end portion longitudinal axis 76 about 25 mm. The proximal end portion 70 transitions to the intermediate portion 74 through a proximal bend 82 and the intermediate portion 74 transitions to the distal end portion 72 through a distal bend 84. In the illustrated embodiment, the proximal bend 82 and the distal bend 84 are both angled internally 135 degrees.

Figure 4:
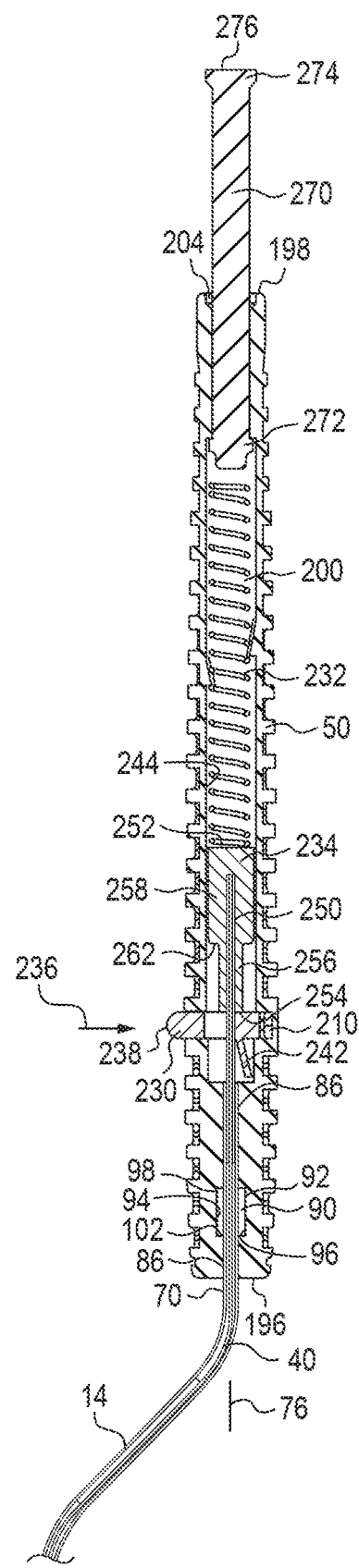
FIG. 4 is a cross-sectional view of an upper portion of the suturing device of FIG. 1 with a plunger in an extended position.

With reference to FIG. 4, the proximal end portion 70 of the elongate body 14 is received in an elongate body passage 86 provided in the handle 50. The elongate body passage 86 has a configuration in cross section normal to the proximal end portion longitudinal axis 76 nearly identical (and only slightly larger, if desired) to the proximal end portion 70 of the elongate body 14. The elongate body 14 and the needle holder 16 are rotatable with respect to the handle 50 about a rotational axis, which in the illustrated embodiment is coaxial with the proximal end portion longitudinal axis 76; however, rotation of the elongate body 14 and the needle holder 16 with respect to the handle 50 requires a greater amount of force to be applied on the elongate body 14 or needle holder 16 than the force that is typically applied to the elongate body 14 or the needle holder 16 while a surgeon is using the suturing device 10 during a suturing procedure.

In the illustrated embodiment, an elongate body retainer 90 connects with the handle 50 and is configured to allow for rotation of the elongate body 14 with respect to the handle 50 about the rotational axis 76. The elongate body retainer 90 also connects with the handle 50 so as to preclude translational movement of the elongate body 14 with respect to the handle 50 along or parallel to the rotational axis 76.

In the illustrated embodiment, the elongate body retainer 90 is barrel shaped element having a diameter that is greater than the diameter of the proximal end portion 70. The elongate body retainer 90 is fixed to the elongate body 14 at the proximal end portion 70 so as to rotate along with the elongate body 14. The elongate body retainer 90 is received in the handle 50. The elongate body retainer 90 has an outer surface 92 that is circular in a cross section taken normal to the rotational axis 76 and is received in an elongate body retainer cavity 94 provided in the handle 50. The elongate body retainer cavity 94 has an inner surface 96 that is also circular in a cross section taken normal to the rotational axis 76.

The outer surface 92 of the elongate body retainer 90 contacts the inner surface 96 of the elongate body retainer cavity 94 so that the elongate body 14 and the needle holder 16 move and rotate along with the handle 50 as the handle 50 is moved and rotated. The interface between the outer surface 92 of the elongate body retainer 90 and the inner surface 96 of the elongate body retainer cavity 94 allows for rotation of the elongate body retainer 90, and thus the elongate body 14 and the needle holder 16, with respect to the handle 50 when an operator grasps the handle 50 to preclude its rotation while rotating the elongate body 14 or the needle holder 16. The elongate body passage 86 transitions to the elongate body retainer cavity 94 at an upper shoulder 98, and the elongate body retainer cavity 94 transitions back to the elongate body passage 86, which is smaller in diameter, at a lower shoulder 102. The upper shoulder 98 and the lower shoulder 102 preclude translational movement of the elongate body retainer 90, and thus the elongate body 14 and the needle holder 16, with respect to the handle 50.

The needle holder 16 extends away from the distal end portion 72 or is provided as part of the distal end portion 72 of the elongate body 14. With reference to FIG. 3, the needle holder 16 is a hollow tubular member. In the illustrated embodiment, a portion of the needle holder 16 that is aligned with the distal end portion longitudinal axis 78 is received inside the elongate body 14; however, the needle holder 16 could be formed as part of the elongate body, e.g., both the elongate body 14 and the needle holder 16 could be made from one tubular stock material. The needle holder 16 depicted in the illustrated embodiment is a curved needle holder that generally follows a constant radius such that the suturing device 10 can have J-hook configuration at a distal end thereof. In the illustrated embodiment, the needle holder 16 is not intended to be removable from the elongate body 14; however, in an alternative arrangement the needle holder 16 can selectively connect with the elongate body 14 via a mechanical connection such as a friction fit or a bayonet connection.

With reference to FIG. 3, the needle holder 16 includes a distal end section 140 having a distal-most tip 142. The needle holder 16 defines a needle passage 144 that is in communication with the track 120 and a distal opening 146. The distal opening 146 is offset from the distal end portion longitudinal axis 78 in a forward direction. In the embodiment depicted in FIG. 3, at least a portion of the suture 22 extends along the needle passage 144 from the second end 32 of the needle 20 toward the distal opening 146 between the needle 20 and an inner surface 152 of the needle holder 16 when the needle 20 is received in the needle passage 144 and the actuator 12 is in the first operating position. The distal-most tip 142 is offset from the distal end portion longitudinal axis 78 in a direction perpendicular from the distal end portion longitudinal axis 78 a distance of less than 7 mm. Common tubular retractors used during minimally invasive spinal surgery procedures have diameters measuring between 14 mm to 22 mm. By spacing the distal-most tip 142 offset from the distal end portion longitudinal axis 78 less than 7 mm, the surgeon can locate the elongate body 14 along the central axis of the tubular retractor and rotate the suturing device around the central axis without contacting the side of the tubular retractor.

Figure 5:
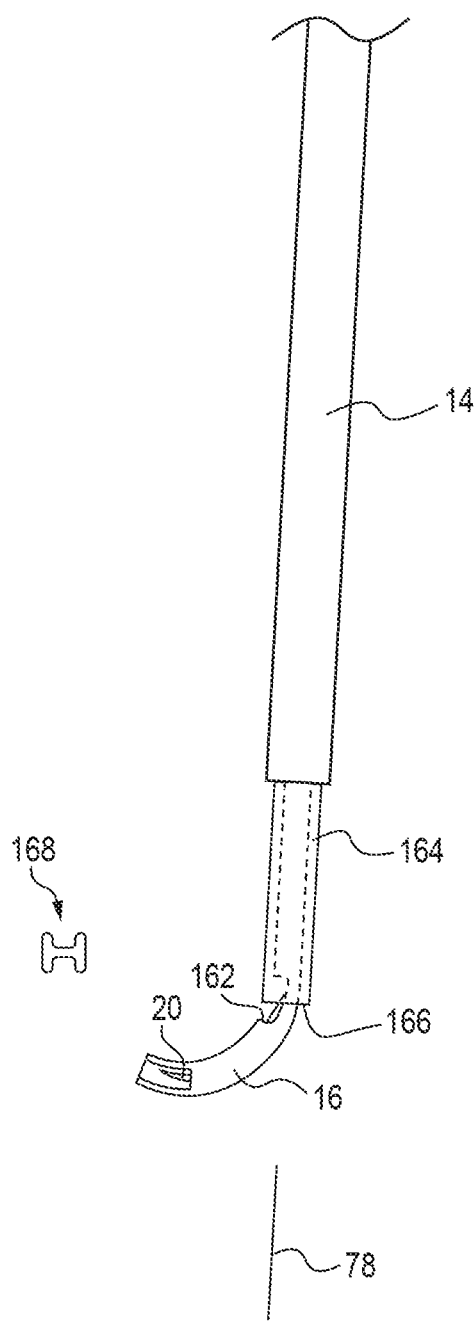
FIG. 5 is a side view of the lower portion of the suturing device of FIG. 1.

As more clearly seen in FIG. 5, the needle holder 16 includes a notch 160. With reference back to FIG. 3, as the needle 20 advances in the advance direction 36, the first end 30 of the needle 20 can pass through target tissue to be sutured. By providing the notch 160, the second end 32 of the needle 20 need not travel past the distal-most tip 142 of the needle holder 16 before being released from the needle holder 16. Such a configuration of the distal opening 146 also facilitates loading of the needle 20 and the suture 22 into the needle passage 144, which occurs by inserting the second end 32 of the needle 20 into the distal opening 146 and moving the needle 20 with respect to the needle holder 16 in a direction opposite to the advance direction 36. The configuration of the distal opening 146 also mitigates the likelihood that the first end 30 of the needle 20 may pass through the suture 22 when being passed through the target tissue 24.

Figure 6:
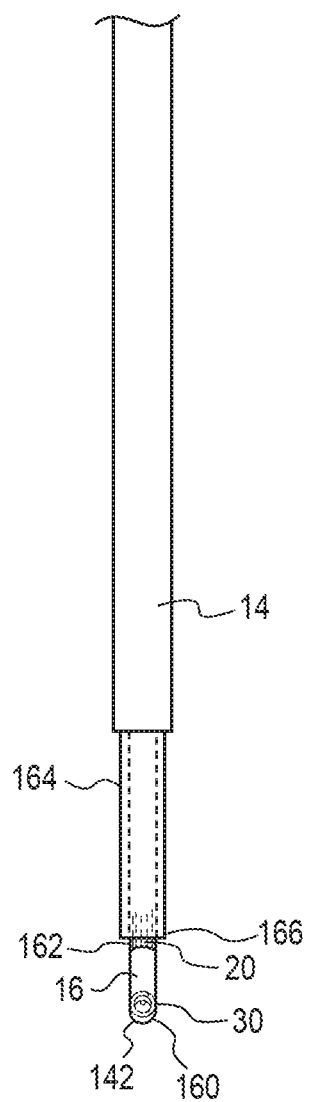
FIG. 6 is a front view of the lower portion of the suturing device of FIG. 1.

The notch 160 is depicted on the side of the needle holder 16, however, the notch 160 can be located elsewhere. By providing the notch 160, the distal opening 146 is non-circular. The distal-most tip 142 can also be rounded (see FIG. 6), which allows for the surgeon to grab or "hook" the target tissue, which is to be sutured, on an internal side thereof and indent the target tissue with the distal-most tip 142 while not catching the target tissue with the first (pointed) end 30 of the needle 20.

Figure 12:
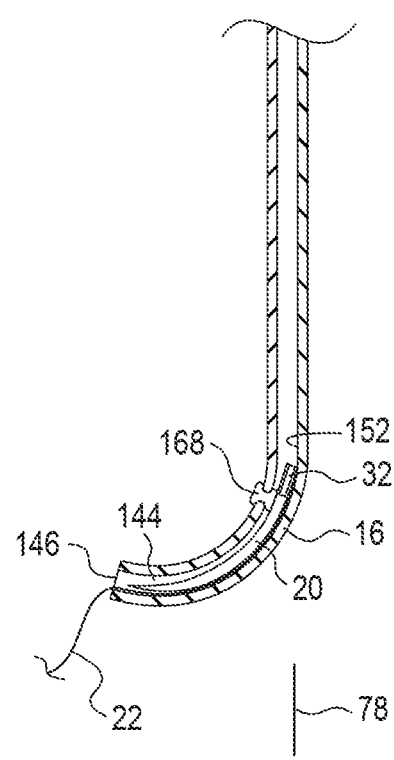
FIG. 12 is a cross-sectional view of a lower portion of a suturing device having a needle retainer.
Figure 13:
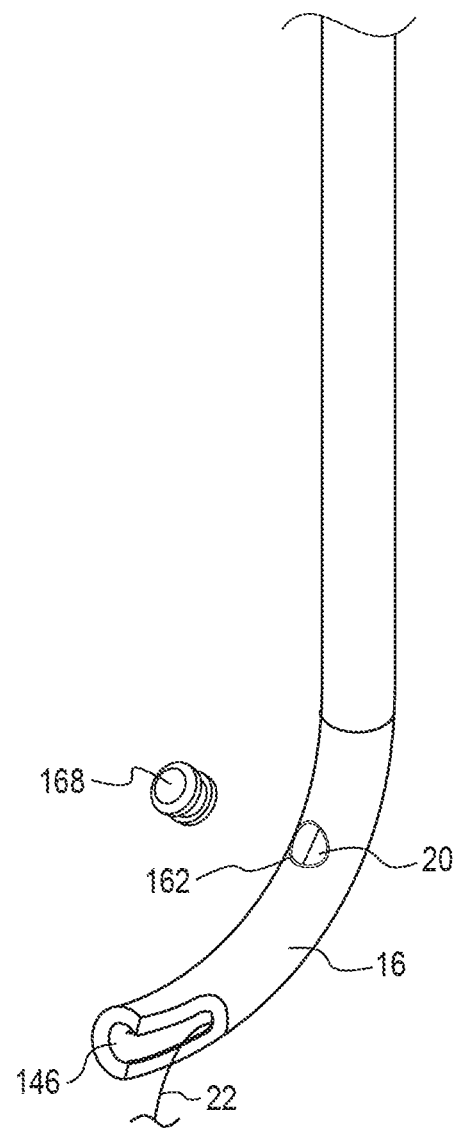
FIG. 13 is a perspective view of the suturing device and needle retainer shown in FIG. 12.

The needle holder 16 also includes a proximal hole 162 spaced from the distal opening 146. In the illustrated embodiment, the proximal hole 162 is located where the needle holder 16 begins to curve away from the distal end portion longitudinal axis 78. The proximal hole 162 is located on an inner side of the curve in the illustrated embodiment. As illustrated, the needle passage 144 is curved following a needle passage radius (not shown), and the needle 20 is a curved needle. The proximal hole 162 is located through a section of the needle holder 16 nearest to the center of the needle passage radius, which can be seen in FIGS. 5 and 12. The proximal hole 162 extends into the needle passage 144 near where the second end 32 of the needle 20 resides when the needle 20 in the retracted position.

A needle retainer can be provided to retain the needle 20 within the needle passage 144 to inhibit unintended movement of the needle 20 with respect to the needle holder 16. One example of such a needle retainer is a flexible sleeve 164 that can be made from a resilient material. The flexible sleeve 164 surrounds the needle holder 16 and terminates at a lower end 166, which extends into the proximal hole 162 to retain the second end 32 of the needle 20 against the inner surface 152 of the needle holder 16 when the needle 20 is received in the needle passage 144 in the retracted position. An entirety of the flexible sleeve 164 can be made from a resilient material, or the portion of the flexible sleeve 164 that extends into the needle passage 144 through the proximal hole 162 may be made from the resilient material. When the actuator 12 is moved from the first operating position to the second operating position, the wire 40 in the illustrated embodiment presses against the second end 32 of the needle 20 overcoming the retaining force of the lower end 166 of the flexible sleeve 164 and moves the needle 20 in the advance direction 36.

Other types or configurations of a needle retainer can be inserted into the proximal hole 162, for example a resilient barbell shaped retainer 168 (FIG. 5), to retain the needle 20 within the needle holder 16. In this alternative arrangement and with reference to FIG. 12, when the resilient barbell shaped retainer 168 is inserted into the proximal hole 162, the resilient barbell shaped retainer 168 presses the second end 32 of the needle 20 against the inner surface 152 of the needle holder 16 when the needle 20 is received in the needle passage 144 in the retracted position. An entirety of the resilient barbell shaped retainer 168 can be made from a resilient material, or the portion of the resilient barbell shaped retainer 168 that extends into the needle passage 144 through the proximal hole 162 may be made from the resilient material, while other components may be made from a more rigid material. When the actuator 12 is moved from the first operating position to the second operating position, the wire 40 in the illustrated embodiment presses against the second end 32 of the needle 20 overcoming the retaining force of the resilient barbell shaped retainer 168 and moves the needle 20 in the advance direction 36.

The needle holders such as the flexible sleeve 164 and the resilient barbell shaped retainer 168 can be used with other types of suturing devices having a needle and a needle holder.

The handle 50 connects with the proximal end portion 70 of the elongate body 14 and is fixed to the elongate body 14 such that movement of the handle 50, e.g., rotational or translational movement, results in the same movement of the elongate body 14, except for when a rotational force on the elongate body 14 overcomes the frictional force between the outer surface 92 of the elongate body retainer 90 and the inner surface 96 of the elongate body retainer cavity 94. The elongate body passage 86 extends from a distal handle end 196 toward a proximal handle end 198 and is aligned with the proximal end portion longitudinal axis 76. The elongate body passage 86 in the illustrated embodiment does not extend all the way from the distal handle end 196 to the proximal handle end 198. In addition to the elongate body retainer cavity 94, the handle 50 also includes an actuator cavity 200, which has a larger diameter than the elongate body passage 86 and the elongate body passage 86 transitions into the actuator cavity 200 moving from the distal handle end 196 towards the proximal handle end 198. The actuator cavity 200 transitions into a reduced diameter passage 202, which transitions into a plunger head recess 204 at the proximal handle end 198. Barbs 206 extend inwardly into the actuator cavity 200, and will be described in more detail below. The handle 50 also includes a manually operated member hole 208 extending into the handle 50 from an outer side surface 212 of the handle 50 into the actuator cavity 200. The handle 50 also includes a manually operated member recess 210 aligned with the manually operated member hole 208 in a direction perpendicular to the proximal end portion longitudinal axis 76.

The outer side surface 212 extends between the proximal handle end 198 and the distal handle end 196. The outer side surface 212 follows a surface of revolution about the proximal end portion longitudinal axis 76 along at least a majority of the handle 50 between the proximal handle end 198 and the distal handle end 196. In the illustrated embodiment, the outer side surface 212 is generally cylindrical along at least the majority of the handle 50 between the proximal handle end 198 and the distal handle end 196. The maximum outer diameter of the handle 50, which can also be referred to as a width measured perpendicular to the proximal end portion longitudinal axis 76 since the handle 50 need not be circular in a cross section normal to the proximal end portion longitudinal axis 76, can be 10-20 mm. In the illustrated embodiment, the handle 50 has a width measured perpendicular to the proximal end portion longitudinal axis 76 of less than 12 mm. Common tubular retractors used during minimally invasive surgery procedures have inner diameters measuring between 14 mm to 22 mm. The maximum width of the handle 50 is not too large, which could impede the line of sight for the surgeon during a surgical procedure, especially when the surgeon is working through a tubular retractor or another small surgical portal other than a tubular retractor. The handle 50 measures about 12-13 cm from the proximal handle end 198 to the distal handle end 196, which allows the surgeon to hold the suturing device similar to a pencil with the portion of the handle 50 near the proximal handle end 198 resting in the space between the forefinger and thumb of the surgeon.

With reference back to FIG. 1, the handle 50 also includes rotation gripping surfaces, which in the illustrated embodiment includes a first rotation gripping surface 220 and a second rotation gripping surface (not visible in FIG. 1), each of which are nearer to planar as compared to the majority of the outer side surface 212 of the handle 50, which follows the surface of revolution. The first rotation gripping surface 220 is diametrically opposed from the second rotation gripping surface. The rotation gripping surfaces 220 can be gripped by an operator while the operator rotates the elongate body 14 with respect to the handle 50. Also, indicia, such as an arrow 222, can be provided on the handle 50 to indicate to the operator that the elongate body 14 can be rotated with respect to the handle 50.

The actuator 12 interacts with the elongate body 14 and is operable between the first operating position and the second operating position. The actuator 12 is configured such that movement of the actuator 12 from the first operating position toward the second operating position moves the needle 20 in the advance direction 36. With reference to FIG. 2, the actuator 12 includes a manually operated member 230, a biasing mechanism 232, and a slider 234.

The manually operated member 230 is operatively connected with the biasing mechanism 232 (through the slider 234 in the illustrated embodiment) so as to preclude the biasing mechanism 232 from moving the actuator 12 toward the second operating position until after the manually operated member 230 has been moved from a non-actuated position (shown in FIGS. 4 and 7) toward an actuated position where the manually operated member 230 is depressed in the direction of arrow 236. The manually operated member 230 includes an operator contact surface 238, which is concave in the illustrated embodiment. The handle 50 includes the outer side surface 212, which is convex in the illustrated embodiment, and the operator contact surface 238 is concave to provide an indication of the location of the operator contact surface 238 by touch, as opposed to sight. Moreover, the operator contact surface 238 extends outwardly from a widest diameter of the outer side surface 212 of the handle 50 to also facilitate location of the operator contact surface 238. The manually operated member 230 operates as a push button in the illustrated embodiment whereby an operator, such as a surgeon, depresses the manually operated member 230 in the direction of arrow 236 moving the manually operated member 230 from the non-actuated position toward the actuated position in which a portion of the manually operated member 230 is received in the manually operated member recess 210 provided in the handle 50. The manually operated member 230 also includes a finger 242 which contacts an inner side surface 244 of the actuator cavity 200 to bias the manually operated member 230 toward the non-actuated position. As more clearly seen in FIG. 8, the manually operated member 230 includes a slider opening made up of a main portion 246 and a smaller portion 248.

With reference back to FIG. 4, the biasing mechanism 232 in the illustrated embodiment is a spring. The spring 232 is a compression spring that is configured to apply a force between 3N and 15N to the slider 234, which is operatively connected with the wire 40, which pushes the needle 20 in the advance direction 36. More particularly, the spring 232 can be configured to apply a force between 9N and 11N to the slider 234. Limiting the force provided by the spring 232, or other biasing mechanism, reduces the likelihood of too great a force being applied to advance the needle 20 so that the needle 20 can pass through the target tissue while still being easily located by the surgeon during a suturing procedure. Even though a compression spring is depicted in the illustrated embodiment, other types of biasing mechanisms, for example a pneumatic-type spring, could be utilized to advance the actuator 12 so as to deploy the needle 20.

The slider 234 includes a wire bore 250, which receives the wire 40 to connect the wire 40 with the slider 234. The wire 40 is fixed to the slider 234 such that movement of the slider 234 results in movement of the wire 40. The slider 234 includes a biasing mechanism contact surface 252, which is an upper end surface as depicted in FIG. 4. The slider 234 also includes a manually operated member contact surface 254, which is a lower surface of the slider 234 as illustrated in FIG. 4. The slider 234 also includes a reduced cross-sectional portion 256 extending from a relatively larger cross-sectional portion 258. The relatively larger cross-sectional portion has a diameter slightly smaller than the inner diameter of the actuator cavity 200 to allow for translational movement of the slider 234 within the actuator cavity 200.

With reference back to FIG. 8, the main portion 246 of the slider opening is configured to receive the reduced cross-sectional portion 256 of the slider 234 when the main portion 246 of the slider opening is aligned with the reduced cross-sectional portion 256. This occurs when the operator presses the operator contact surface 238 in the direction of arrow 236 thus moving the manually operated member 230 to the right per the orientation shown in FIGS. 4 and 7. The main portion 246 of the slider opening, however, is smaller than the relatively larger cross-sectional portion 258 of the slider 234. Accordingly, the travel distance of the slider 234 is limited by the distance between manually operated member contact surface 254 and a shoulder 262 where the reduced cross-sectional portion 256 transitions to the relatively larger cross-sectional portion 258.

With reference back to FIG. 8, the smaller portion 248 of the slider opening is configured to allow for passage of the wire 40 to allow for the connection of the wire 40 to the slider 234. When the manually operated member is in the non-actuated position (shown in FIGS. 4 and 7), the manually operated member 230 contacts the slider 234 to preclude movement of the slider 234 with respect to the manually operated member 230. When an operator moves the manually operated member 230 in the direction of arrow 236, the manually operated member 230 is moved in the direction of arrow 236 which allows the main portion 246 of the slider opening to align with the reduced cross-sectional portion 256 of the slider, and the biasing mechanism 232 moves the slider 234 downwardly (per the orientation shown in FIGS. 4 and 7) such that the reduced cross-sectional portion 256 passes through the main portion 246 of the slider opening thus moving the wire 40 and thus moving the needle 20 in the advance direction 36.

Figure 7:
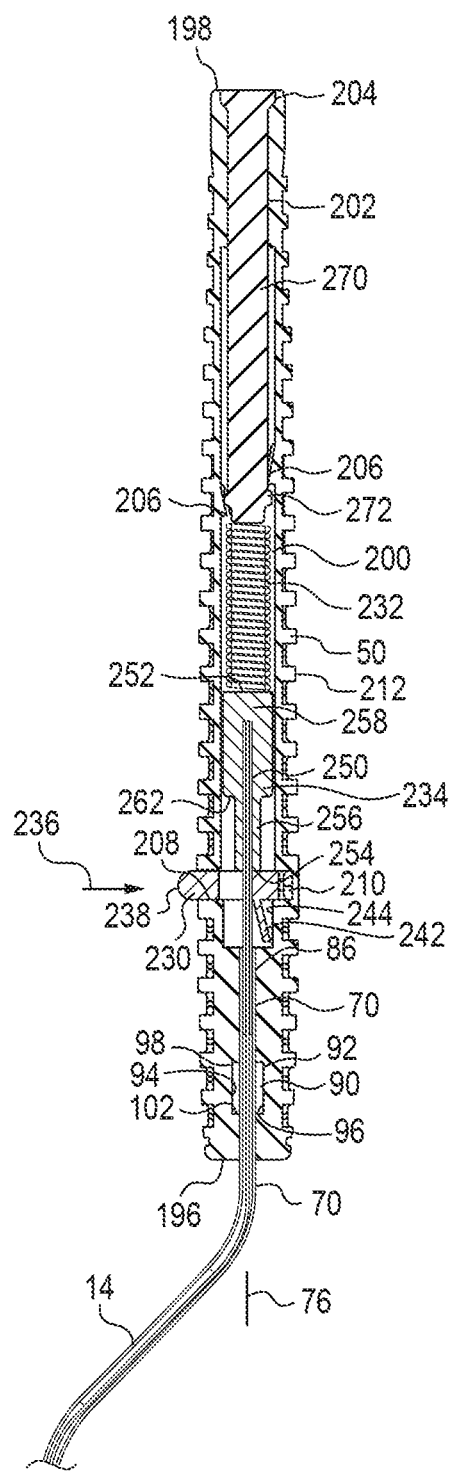
FIG. 7 is a cross-sectional view of the upper portion of the suturing device of FIG. 1 with a plunger in a depressed position.
Figure 8:
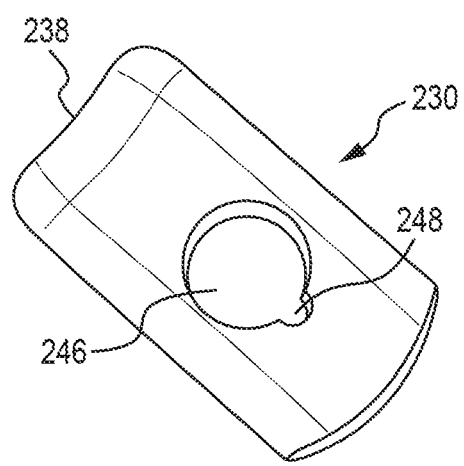
FIG. 8 is a perspective view of a manually operated member for the suturing device of FIG. 1.

The suturing device 10 also includes a plunger 270 connected with the handle 50 and movable with respect to the handle 50 between an extended position (FIGS. 1 and 4) and a depressed position (FIG. 7). Movement of the plunger 270 from the extended position to the depressed position compresses the spring 232. The plunger 270 includes a distal annular shoulder 272 that operates as a locating feature for the spring 232 and also as a retaining feature to retain the plunger 270 in the depressed position. With reference back to FIG. 7, when the plunger 270 is in the depressed position the distal annular shoulder 272 engages the barb 206 and the barb 206 counteracts the upward (per the orientation shown in FIG. 7) on the plunger 270 from the spring 232. When the spring 232 is compressed by the plunger 270 with the plunger 270 in the depressed position shown in FIG. 7, the spring 232 is configured to apply a force between 3 N and 15 N, and more particularly between 9 N and 11 N to the plunger 270 and to the slider 234. The plunger 270 can cooperate with the spring 232, or other biasing mechanism, to vary the biasing force of the spring 232. For example, another barb could be provided between the barb 206 depicted in FIG. 4 and the proximal handle end 198. Where FIG. 7 depicts a fully depressed position for the plunger 270, if the distal annular shoulder 272 were retained by the barb between the barb 206 depicted in FIG. 4 and the proximal handle end 198 in an intermediate depressed position, a smaller biasing force would be applied by the spring 232 as compared to the biasing force when the plunger 270 is in the fully depressed position. Alternatively, where the biasing mechanism is air, for example, the distal annular shoulder 272 could include a seal that contacts the inner side surface 244 of the actuator cavity 200 varying the volume of air above the slider 234 thus varying the pressure exerted by the air on the slider 234.

The spring 232 can be configured such that very little, if any, force is applied by the spring 232 on the slider 234 when the plunger 270 is in the extended position. The operator then primes the suturing device by depressing the plunger 270. A head 274 of the plunger 270 can be received in the plunger head recess 204 so that an upper surface 276 of the plunger 270 is flush with the proximal handle end 198 to provide an indication that the device is ready to be actuated. If desired, however, the manually operated member 230 can be moved from the non-actuated position to the actuated position with the plunger 270 in the extended position, and then the plunger 270 can be depressed to advance the needle 20. Actuation via this method will not be as quick as when the plunger 270 is first depressed and then the manually operated member is next depressed.

Figure 9:
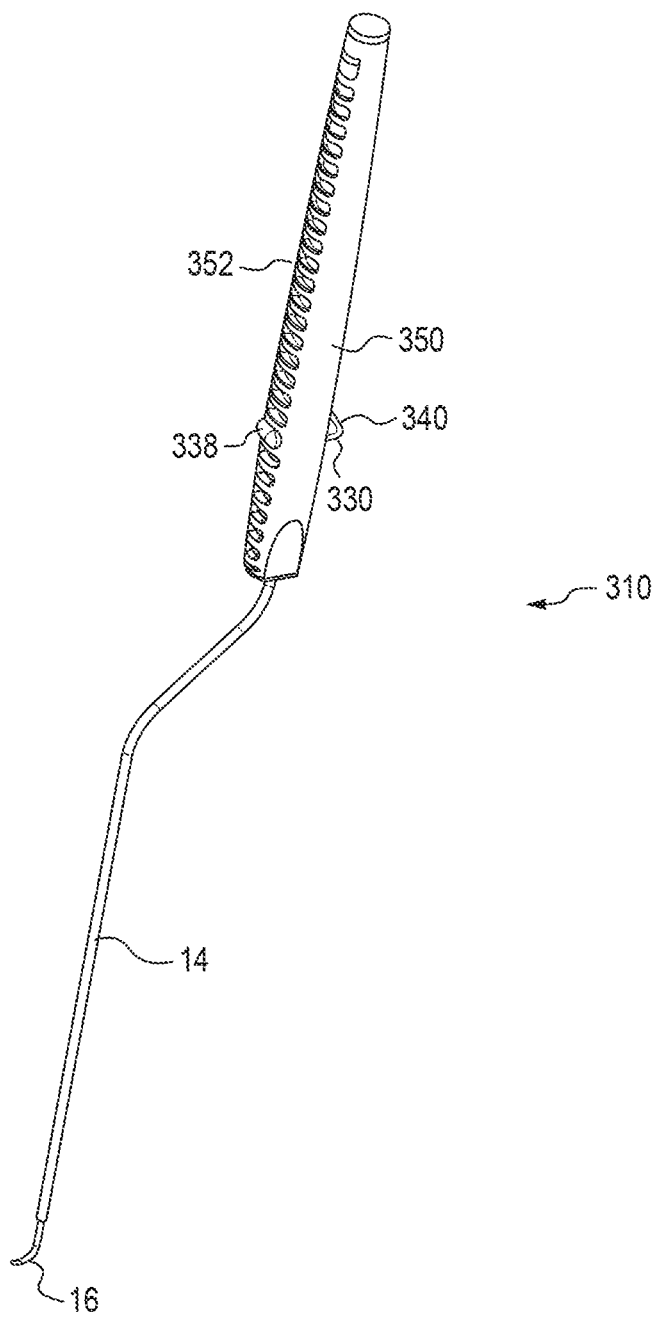
FIG. 9 is a perspective view of an alternative suturing device.
Figure 10:
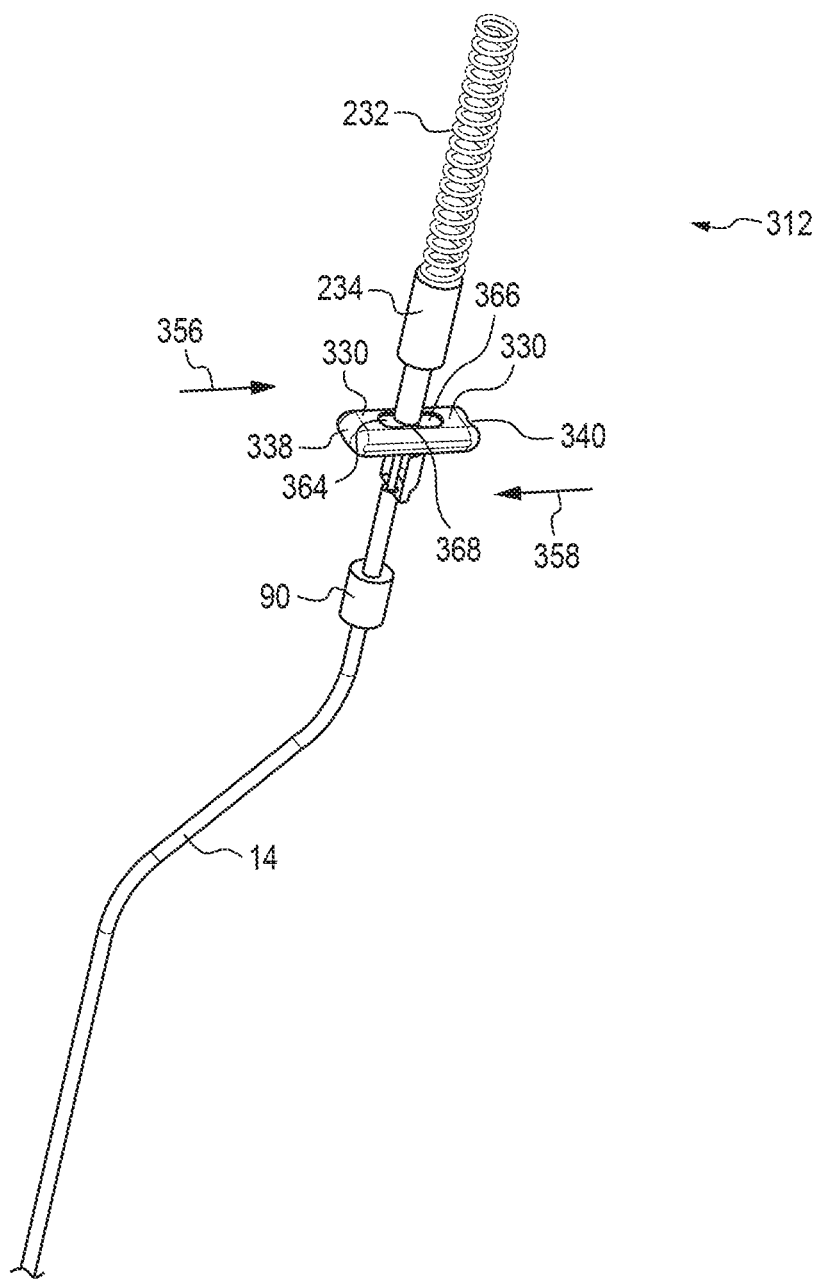
FIG. 10 is a perspective view an upper portion of the suturing device of FIG. 9 with a handle removed to show components of an actuator.
Figure 11:
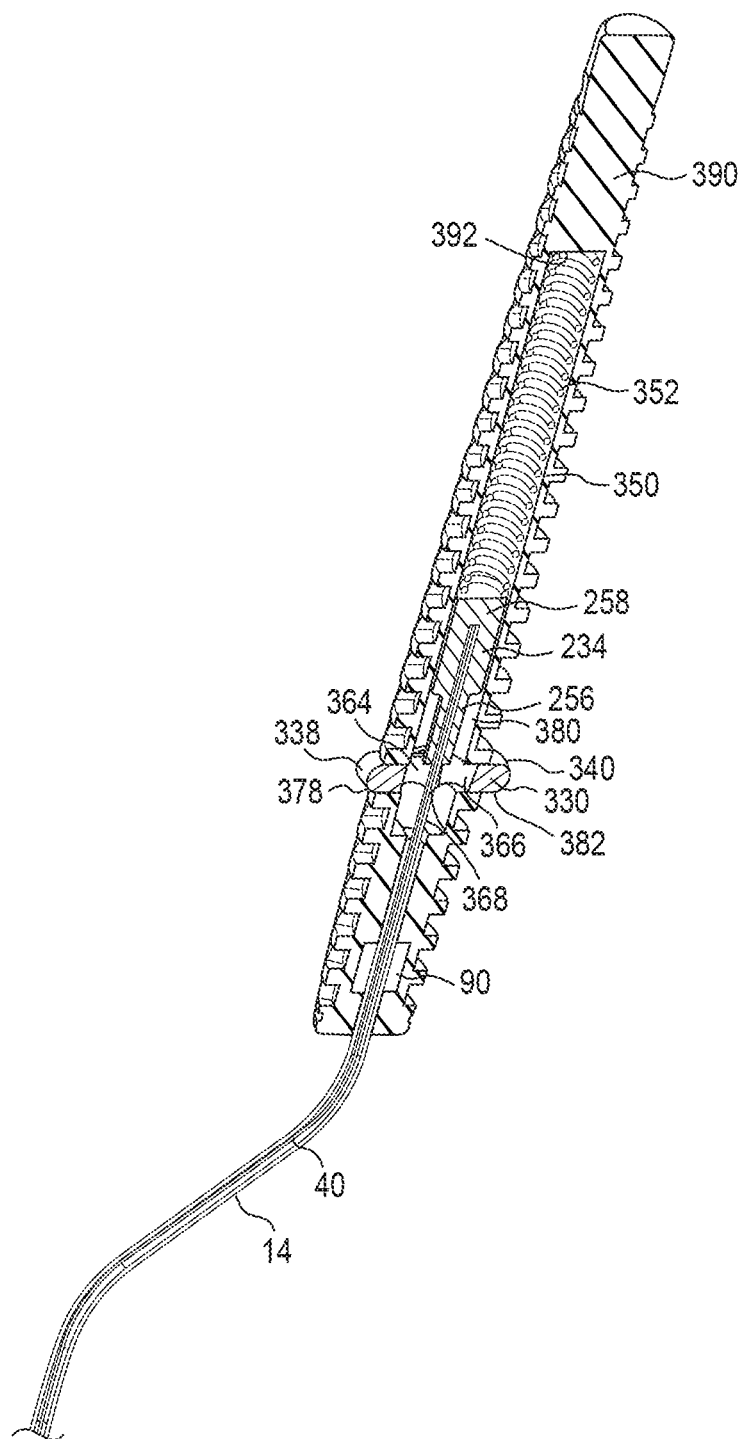
FIG. 11 is a cross-sectional view of an upper portion of the suturing device of FIG. 9.

FIGS. 9-11 depict an alternative suturing device including an actuator 312 that differs from the actuator depicted in FIG. 1, while including the same elongate body 14 and needle holder 16. With reference to FIG. 10, actuator 312 interacts with the elongate body 14 and is operable between a first operating position and a second operating position. The actuator 312 is configured such that movement of the actuator 312 from the first operating position toward the second operating position moves the needle 20 in the advance direction 36. The actuator 312 includes a manually operated member 330, which differs from the manually operated member 230, a biasing mechanism 232, which is a spring and can be the same as the spring 232 described above, and a slider 234, which is the same as the slider 234 described above.

The manually operated member 330 is operatively connected with the biasing mechanism 232 (through the slider 234 in the illustrated embodiment) so as to preclude the biasing mechanism 232 from moving the actuator 12 toward the second operating position until after the manually operated member 330 has been moved from a non-actuated position toward an actuated position. The manually operated member 330 differs from the manually operated member 230 described above in that the manually operated member 330 is bi-directional. The manually operated member 330 includes a first operator contact surface 338, which is concave in the illustrated embodiment, a second operator contact surface 340, which is also concave in the illustrated embodiment and on an opposite side of the manually operated member 330.

With reference back to FIG. 9, the suturing device 310 also includes a handle 350 that differs from the handle 50 described above. The differences between the handle 350 and the handle 50 will be described with the understanding that the other portions of the handles are similar. An outer side surface 352 of the handle 350 is convex in the illustrated embodiment, and both operator contact surfaces 338, 340 are concave to provide an indication of the location of the operator contact surfaces 338, 340. Both operator contact surfaces 338, 340 extend outwardly from a widest diameter of the outer side surface 352 of the handle 350 to also facilitate their location. The manually operated member 330 operates as a push button in the illustrated embodiment whereby an operator, such as a surgeon, depresses the first operator contact surface 338 in the direction of arrow 356, or the surgeon depresses the second operator contact surface 340 in the direction of arrow 358 moving the manually operated member 330 from the non-actuated position toward the actuated position. The manually operated member 330 includes a slider opening made up of a first outer portion 364 nearer to the first operator contact surface 338, a second outer portion 366 nearer to the second operator contact surface 340 and a smaller central portion 368 between the first outer portion 364 and the second outer portion 366.

The first outer portion 364 and the second outer portion 366 of the slider opening are each configured to receive the reduced cross-sectional portion 256 of the slider 234 when properly aligned with the reduced cross-sectional portion 256. This occurs when the operator presses the first operator contact surface 338 in the direction of arrow 356 thus moving the manually operated member 330 to the right per the orientation shown in FIG. 10, or when the operator presses the second operator contact surface 340 in the direction of arrow 358 thus moving the manually operated member 330 to the left per the orientation shown in FIG. 10. Both the first outer portion 364 and the second outer portion 366 of the slider opening, however, are smaller than the relatively larger cross-sectional portion 258 of the slider 234. The smaller central portion 368 of the slider opening is configured to allow for passage of the wire 40 to allow for the connection of the wire 40 to the slider 234. When the manually operated member is in the non-actuated position, the manually operated member 230 contacts the slider 234 to preclude movement of the slider 234 with respect to the manually operated member 230.

The handle 350 includes a first manually operated member hole 378 extending into the handle 350 from the outer side surface 352 of the handle 350 into an actuator cavity 380, which is similar in configuration to the actuator cavity 25 described above. The handle 350 also includes a second manually operated member hole 382 extending into the handle 350 from the outer side surface 352 of the handle 350 into an actuator cavity 380. The suturing device 310 does not include a plunger like the plunger 270 described above. Accordingly, the handle 350 includes a closed proximal end portion 390, which defines a spring contact surface 392 against which the spring acts.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A suturing device comprising:
an elongate body including a proximal end portion and a distal end portion;
a needle holder extending away from the distal end portion or provided as part of the distal end portion of the elongate body, the needle holder including a distal end section having a distal-most tip, the needle holder defining a needle passage and a distal opening adjacent the distal-most tip, wherein the needle passage is curved, wherein the needle holder includes a proximal hole extending into the needle passage, wherein the proximal hole is spaced from the distal opening;
a needle in the needle passage, the needle including a first end, which is pointed, and a second end, which is opposite the first end, wherein the needle is a curved needle;
an actuator interacting with the elongate body and operable between a first operating position and a second operating position, wherein the actuator is configured such that movement of the actuator from the first operating position toward the second operating position moves the needle in an advance direction; and
a needle retainer engaging the needle holder and the needle when the actuator is in the first operating position and configured to inhibit movement of the needle toward the distal opening while the actuator is in the first operating position, wherein a portion of the needle retainer extends into the needle passage through the proximal hole.

2. The suturing device of claim 1, wherein the needle passage is curved following a needle passage radius, and the needle is a curved needle.

3. The suturing device of claim 2, wherein proximal hole is located through a section of the needle holder nearest to the center of the needle passage radius.

4. The suturing device of claim 2, wherein the proximal hole is located where the needle holder begins to curve away from a distal end portion longitudinal axis of the elongate body.

5. The suturing device of claim 4, wherein the elongate body has a bayonet configuration.

6. The suturing device of claim 1, wherein the portion of the needle retainer extending into the needle passage through the proximal hole is made from a resilient material.

7. The suturing device of claim 6, wherein an entirety of the needle retainer is made from the resilient material.

8. The suturing device of claim 6, wherein the needle retainer is a flexible sleeve that surrounds the needle holder and terminates at a lower end, which extends into the proximal hole.

9. The suturing device of claim 6, wherein the needle retainer is a resilient barbell shaped retainer.

10. The suturing device of claim 1, wherein the needle retainer is a flexible sleeve that surrounds the needle holder and terminates at a lower end, which extends into the proximal hole.

11. The suturing device of claim 1, wherein the needle retainer is a resilient barbell shaped retainer having a portion extending into the proximal hole.

12. The suturing device of claim 1, wherein the needle moves from a retracted position toward a released condition as the actuator moves from the first operating position toward the second operating position, and the proximal hole extends into the needle passage near where the second end of the needle resides when the needle in the retracted position.

13. The suturing device of claim 12, further comprising a suture extending from the second end of the needle.

14. The suturing device of claim 13, wherein the suture extends through the distal opening when the needle is in the retracted position and the actuator is in the first operating position.

* * * * *